United States Patent
Dack et al.

(10) Patent No.: US 10,538,523 B2
(45) Date of Patent: Jan. 21, 2020

(54) 4-(BIPHEN-3-YL)-1H-PYRAZOLO[3,4-C] PYRIDAZINE DERIVATIVES OF FORMULA (I) AS GABA RECEPTOR MODULATORS FOR USE IN THE TREATMENT OF EPILEPSY AND PAIN

(71) Applicant: PFIZER LIMITED, Sandwich, Kent (GB)

(72) Inventors: Kevin Neil Dack, Sandwich (GB); Robert McKenzie Owen, Great Abington (GB); David Cameron Pryde, Great Abington (GB)

(73) Assignee: PFIZER LIMITED, Sandwich, Kent (GB)

( * ) Notice: Subject to any disclaimer, the term of this patent is extended or adjusted under 35 U.S.C. 154(b) by 0 days.

(21) Appl. No.: 15/777,678

(22) PCT Filed: Nov. 22, 2016

(86) PCT No.: PCT/IB2016/057049
§ 371 (c)(1),
(2) Date: May 21, 2018

(87) PCT Pub. No.: WO2017/098367
PCT Pub. Date: Jun. 15, 2017

(65) Prior Publication Data
US 2018/0346470 A1 Dec. 6, 2018

Related U.S. Application Data

(60) Provisional application No. 62/265,572, filed on Dec. 10, 2015.

(51) Int. Cl.
*C07D 487/04* (2006.01)
*A61K 31/5025* (2006.01)
*A61K 45/06* (2006.01)

(52) U.S. Cl.
CPC ........ *C07D 487/04* (2013.01); *A61K 31/5025* (2013.01); *A61K 45/06* (2013.01)

(58) Field of Classification Search
CPC ... C07D 487/04; A61K 31/5025; A61K 45/06
See application file for complete search history.

(56) References Cited

U.S. PATENT DOCUMENTS

2014/0171435 A1* 6/2014 Omoto ............... A61K 31/5025
514/248

FOREIGN PATENT DOCUMENTS

WO WO2015189744 12/2015

* cited by examiner

*Primary Examiner* — Amanda L Aguirre
(74) *Attorney, Agent, or Firm* — Haley Guiliano LLP; James F. Haley, Jr.; Brittany J. Barrett

(57) ABSTRACT

The present invention relates to pyrazolopyridazine derivatives. More particularly, it relates to 4-(biphenyl-3-yl)-1H-pyrazolo[3,4-c]pyridazine derivatives of formula (I), and pharmaceutically acceptable salts thereof, wherein X, $R^1$, $R^2$, $R^3$, $R^4$ and $R^5$ are as defined in the description. The pyrazolopyridazine derivatives of the present invention modulate the activity of the $GABA_A$ receptor. They may useful in the treatment of a number of conditions, including pain and epilepsy.

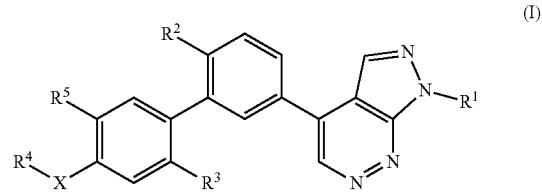

19 Claims, No Drawings

4-(BIPHEN-3-YL)-1H-PYRAZOLO[3,4-C] PYRIDAZINE DERIVATIVES OF FORMULA (I) AS GABA RECEPTOR MODULATORS FOR USE IN THE TREATMENT OF EPILEPSY AND PAIN

This application is a national phase filing under 35 U.S.C. § 371 of international patent application number PCT/IB2016/057049 filed Nov. 22, 2016, which in turn claims the benefit of priority to U.S. Provisional Patent Application Ser. No. 62/265,572 filed Dec. 10, 2018, the disclosure of each of these two applications is hereby incorporated by reference in its entirety.

FIELD OF THE INVENTION

The present invention relates to pyrazolopyridazine derivatives. More particularly, it relates to 4-(biphenyl-3-yl)-1H-pyrazolo[3,4-c]pyridazine derivatives. The pyrazolopyridazine derivatives of the present invention modulate the activity of the $GABA_A$ receptor. They may be useful in the treatment of a number of conditions, including pain and epilepsy.

BACKGROUND

Gamma-aminobutyric acid (GABA) has been identified as a major inhibitory neurotransmitter, and agents that modulate GABAergic neurotransmission are used extensively in the treatment of conditions such as epilepsy, anxiety and depression. Two families of GABA receptor have been described, termed $GABA_A$ and $GABA_B$.

The $GABA_A$ receptor is a member of the ligand-gated ion channel superfamily. The functional receptor generally comprises a number of subunits. At least 16 such subunits have been characterized, including 6 alpha subunits ($\alpha_{1-6}$), 3 beta subunits ($\beta_{1-3}$), 3 gamma subunits ($\gamma_{1-3}$), and delta, epsilon, pi and theta subunits ($\delta$, $\varepsilon$, $\pi$, $\theta$). Most $GABA_A$ receptors are made up of 2 alpha, 2 beta and one gamma subunit. Several drug binding sites have been described. These include the binding site for the endogenous ligand (GABA), and allosteric binding sites. Drugs that bind at the allosteric binding sites may be positive allosteric modulators, which increase responsiveness, negative allosteric modulators, which decrease receptor responsiveness, or neutral, which term refers to compounds that bind to the allosteric binding sites without modulating the activity of the receptor. Recent evidence has suggested that $GABA_A$ receptors comprising either the $\alpha_2$ or $\alpha_3$ subunit (herein termed $GABA_A$ $\alpha_{2/3}$ receptors) may be involved in certain pain states, and that positive allosteric modulators of these receptors may be useful analgesics (Mirza, N. R. and Munro, G., *Drug News and Perspectives*, 2010, 23(6), 351-360).

4-(Biphenyl-3-yl)-1H-pyrazolo[3,4-c]pyridazine derivatives have not been reported as having an interaction with $GABA_A$ $\alpha_{2/3}$ receptors. International patent application PCT/IB2013/60631 (published as WO2014/091368) discloses 4-(biphenyl-3-yl)-7H-imidazo[4,5-c]pyridazine derivatives that have affinity for the $\alpha_2$, $\alpha_3$ and/or $\alpha_5$ subunits.

There is a continuing interest in finding new compounds that interact with $GABA_A$ receptors, and particularly for compounds that have a reduced propensity for causing the adverse events such as drowsiness that are associated with the currently available $GABA_A$ modulators such as benzodiazepines. It is thought that these adverse effects are a result of modulation of $\alpha_1$ subunit-containing receptors, and so preferred compounds will have a high affinity for the $\alpha_{2/3}$ subunit-containing receptors with good efficacy as positive allosteric modulators, while having low efficacy at receptors with other a subunits, particularly the $\alpha_1$ subunit-containing receptors.

These drug candidates should additionally have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile. They should be non-toxic and demonstrate few side-effects. Ideal drug candidates should exist in a physical form that is stable, non-hygroscopic and easily formulated.

SUMMARY OF THE INVENTION

In a first aspect, the present invention provides a compound of formula (I)

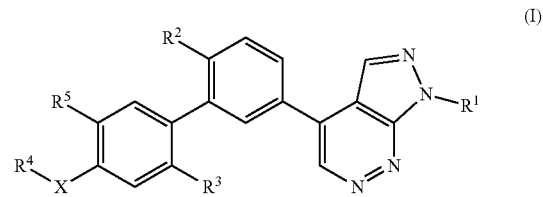

(I)

or a pharmaceutically acceptable salt thereof, wherein
X is selected from —S(O)$_2$— and —C(O)—;
$R^1$ is selected from (C$_2$-C$_4$)alkyl, (C$_3$-C$_5$)cycloalkyl and methyl-substituted (C$_3$-C$_5$)cycloalkyl;
$R^2$ is selected from H, F, Cl, OCH$_3$ and CN;
$R^3$ is selected from H, F, CHF$_2$, OCH$_3$ and CN;
when X is —S(O)$_2$— then
  $R^4$ is selected from (C$_1$-C$_4$)alkyl, (C$_3$-C$_5$)cycloalkyl, NH$_2$ and NH(C$_1$-C$_4$)alkyl, and R$_5$ is H; or
  $R^4$ and $R^5$ together are —CH$_2$CH$_2$— or —N(CH$_3$)CH$_2$—; and
when X is —C(O)— then
  $R^4$ is selected from NH$_2$ and NH(C$_1$-C$_4$)alkyl, and R$_5$ is H; or
  $R^4$ and $R^5$ together are —N(CH$_3$)CH$_2$—.

The compounds of formula (I) and their pharmaceutically acceptable salts are referred to herein as "the compounds of the invention". The definition above is referred to herein as embodiment E1 of this aspect. Further embodiments of this aspect of the invention are described in detail below.

In another aspect, the invention provides for a pharmaceutical composition comprising a compound of formula (I) as described above, or in any one of the preferred embodiments, or a pharmaceutically acceptable salt thereof, and a pharmaceutically acceptable excipient.

In another aspect, the invention provides for a compound of formula (I) as described above, or in any one of the preferred embodiments, or a pharmaceutically acceptable salt thereof, for use as a medicament. In an embodiment according to this aspect the compound of formula (I), or a pharmaceutically acceptable salt thereof, is for use in the treatment of pain. In another embodiment according to this aspect the compound of formula (I), or a pharmaceutically acceptable salt thereof, is for use in the treatment of epilepsy.

In another aspect, the invention provides for a method of treating pain comprising administering a therapeutically effective amount of a compound of formula (I) as described above, or in any one of the preferred embodiments, or a pharmaceutically acceptable salt thereof, to an individual in need of such treatment.

In another aspect, the invention provides for a method of treating epilepsy comprising administering a therapeutically effective amount of a compound of formula (I) as described above, or in any one of the preferred embodiments, or a pharmaceutically acceptable salt thereof, to an individual in need of such treatment.

In another aspect, the invention provides for the use of a compound of formula (I) as described above, or in any one of the preferred embodiments, or a pharmaceutically acceptable salt thereof, for the treatment of pain.

In another aspect, the invention provides for the use of a compound of formula (I) as described above, or in any one of the preferred embodiments, or a pharmaceutically acceptable salt thereof, for the treatment of epilepsy.

In another aspect, the invention provides for the use of a compound of formula (I) as described above, or in any one of the preferred embodiments, or a pharmaceutically acceptable salt thereof, for the manufacture of a medicament for treating pain.

In another aspect, the invention provides for the use of a compound of formula (I) as described above, or in any one of the preferred embodiments, or a pharmaceutically acceptable salt thereof, for the manufacture of a medicament for treating epilepsy.

In another aspect, the invention provides for a combination comprising a compound of formula (I) as described above, or in any one of the preferred embodiments, or a pharmaceutically acceptable salt thereof, and a second pharmaceutically active agent.

DETAILED DESCRIPTION OF THE INVENTION

Alkyl groups, containing the requisite number of carbon atoms, can be unbranched or branched. $(C_1-C_4)$Alkyl includes methyl, ethyl, n-propyl (1-propyl) and isopropyl (2-propyl, 1-methylethyl), n-butyl (1-butyl), sec-butyl (2-butyl, 1-methylpropyl), isobutyl (2-methylpropyl), and tert-butyl (1,1-dimethylethyl).

$(C_3-C_5)$Cycloalkyl includes cyclopropyl, cyclobutyl and cyclopentyl. Methyl-substituted $(C_3-C_5)$cycloalkyl includes 1-methylcyclopropyl, 2-methylcyclopropyl, 1-methylcyclobutyl, 2-methylcyclobutyl, 3-methylcyclobutyl, 1-methylcyclopentyl, 2-methylcyclopentyl and 3-methylcyclopentyl.

For the compounds of the invention where $R^4$ and $R^5$ together are —N(CH$_3$)CH$_2$— it should be understood that —N(CH$_3$)— takes the place of $R^4$ and —CH$_2$— takes the place of $R^5$. When X is —S(O)2- the resulting compound is a sultam

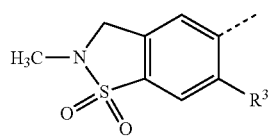

and when X is —C(O)— the resulting compound is a lactam

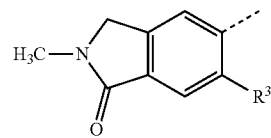

Further specific embodiments of the compounds of the invention are as follows.

In embodiment E2, there is provided a compound according to embodiment E1 of formula ($I^A$)

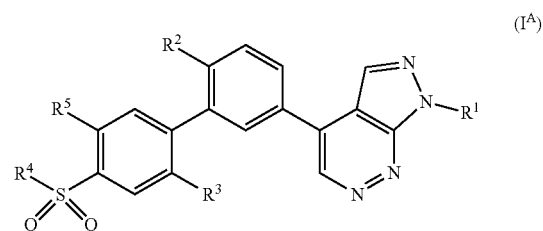

or a pharmaceutically acceptable salt thereof, wherein
$R^1$, $R^2$ and $R^3$ are as defined in claim 1 and
$R^4$ is selected from $(C_1-C_4)$alkyl, $(C_3-C_5)$cycloalkyl, NH$_2$ and NH$(C_1-C_4)$alkyl,
and $R_5$ is H; or
$R^4$ and $R^5$ together are —CH$_2$CH$_2$— or —N(CH$_3$)CH$_2$—.

In embodiment E3, there is provided a compound according to embodiment E2, or a pharmaceutically acceptable salt thereof, wherein $R^4$ is $(C_1-C_4)$alkyl and $R_5$ is H.

In embodiment E4, there is provided a compound according to embodiment E3, or a pharmaceutically acceptable salt thereof, wherein $R^4$ is ethyl.

In embodiment E5, there is provided a compound according to embodiment E1 of formula ($I^B$)

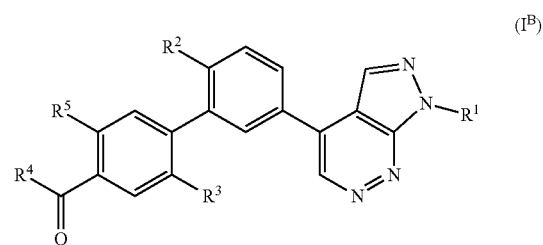

or a pharmaceutically acceptable salt thereof, wherein
$R^1$, $R^2$ and $R^3$ are as defined in claim 1 and
$R^4$ is selected from NH$_2$ and NH$(C_1-C_4)$alkyl, and $R^5$ is H; or
$R^4$ and $R^5$ together are —N(CH$_3$)CH$_2$—.

In embodiment E6, there is provided a compound according to embodiment E5, or a pharmaceutically acceptable salt thereof, wherein $R^4$ and $R^5$ together are —N(CH$_3$)CH$_2$—.

In embodiment E7, there is provided a compound according to any one of embodiments E1, E2, E3, E4, E5 and E6, or a pharmaceutically acceptable salt thereof, wherein $R^1$ is $(C_2-C_4)$alkyl.

In embodiment E8, there is provided a compound according to embodiment E7, or a pharmaceutically acceptable salt thereof, wherein $R^1$ is ethyl.

In embodiment E9, there is provided a compound according to any one of embodiments E1, E2, E3, E4, E5, E6, E7 and E8, or a pharmaceutically acceptable salt thereof, wherein $R^2$ is selected from H and F.

In embodiment E10, there is provided a compound according to embodiment E9, or a pharmaceutically acceptable salt thereof, wherein $R^2$ is F.

In embodiment E11, there is provided a compound according to any one of embodiments E1, E2, E3, E4, E5, E6, E7, E8, E9 and E10, or a pharmaceutically acceptable salt thereof, wherein $R^3$ is selected from H and $OCH_3$.

In embodiment E12, there is provided a compound according to embodiment E11, or a pharmaceutically acceptable salt thereof, wherein $R^3$ is $OCH_3$ Preferred compounds of the invention include:
4-(4'-ethanesulfonyl-6-fluoro-2'-methoxybiphenyl-3-yl)-1-ethyl-1H-pyrazolo[3,4-c]pyridazine,
4-(4'-ethanesulfonyl-6-fluorobiphenyl-3-yl)-1-ethyl-1H-pyrazolo[3,4-c]pyridazine, and
5-[5-(1-ethyl-1H-pyrazolo[3,4-c]pyridazin-4-yl)-2-fluorophenyl]-6-methoxy-2-methyl-2,3-dihydroisoindol-1-one,
and pharmaceutically acceptable salts thereof.

Certain compounds of formula (I) include one or more stereogenic centers and so may exist as optical isomers, such as enantiomers and diastereomers. All such isomers and mixtures thereof are included within the scope of the present invention.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Hemisalts of acids and bases may also be formed, for example, hemisulphate salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K^+$, or —$SO_3^-Na^+$) or non-ionic (such as —$N^-N^+(CH_3)_3$) polar head group. For more information, see *Crystals and the Polarizing Microscope* by N. H. Hartshorne and A. Stuart, 4$^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wlen (Wiley, New York, 1994).

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, nitrogen, such as $^{13}N$ and $^{15}N$, oxygen, such as $^{15}O$, $^{17}O$ and $^{18}O$, and sulphur, such as $^{35}S$.

Certain isotopically-labelled compounds of the invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Tomography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

All of the pyrazolopyridazine derivatives of the formula (I) can be prepared by the procedures described in the general methods presented below or by routine modifications thereof. The present invention also encompasses any one or more of these processes for preparing the pyrazolopyridazine derivatives of formula (I), in addition to any novel intermediates used therein.

According to a first process, compounds of formula (I) may be prepared by the method illustrated in Scheme 1.

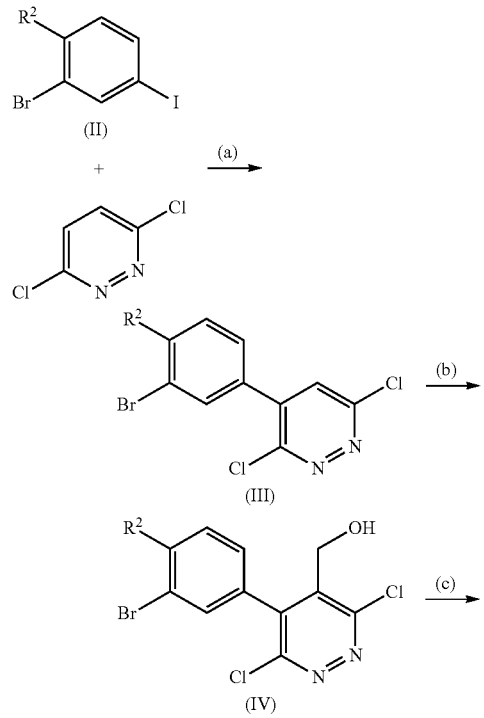

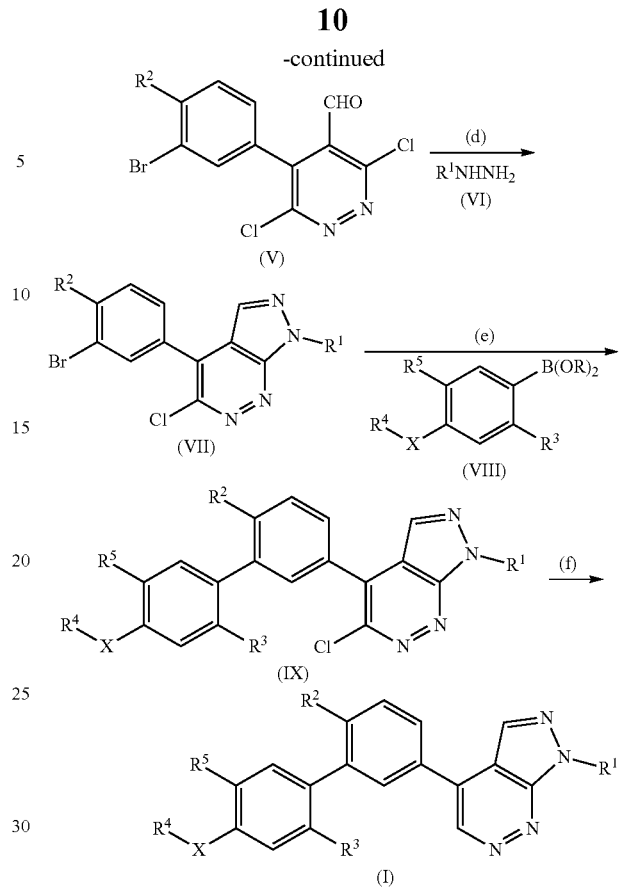

In process step (a), 3,6-dichloropyridazine is coupled to a 4-substituted-3-bromoiodobenzene of formula (II) to provide a 4-aryl-3,6-dichloropyridazine of formula (III). Typically the 3,6-dichloropyridazine is first treated with a zinc reagent such as bis-(2,2,6,6-tetramethylpiperidine)zinc in a suitable solvent such as tetrahydrofuran (THF). The bromoiodobenzene derivative is then added, together with a suitable coupling catalyst, typically a palladium derivative such as bis-(dibenzylideneacetone)-palladium in combination with a phosphine ligand such as tris-(2-furyl)phosphine, and the mixture is stirred until the reaction is judged to be complete and the product is isolated using standard methods.

In process step (b), the 4-aryl-3,6-dichloropyridazine of formula (III) is hydroxymethylated to provide a 4-aryl-3,6-dichloro-5-(hydroxymethyl)pyridazine of formula (IV). Typically the 4-aryl-3,6-dichloropyridazine is reacted with methanol in the presence of an iron(II) salt such as iron(II) sulfate, hydrogen peroxide and a mineral acid such as sulfuric acid. A co-solvent such as dichloromethane may be used. The reaction mixture is generally heated to reflux and stirred until the reaction is judged to be complete and the product is isolated using standard methods.

In process step (c), the 4-aryl-3,6-dichloro-5-(hydroxymethyl)pyridazine of formula (IV) is oxidized to provide a 4-aryl-3,6-dichloropyridazine-5-carbaldehyde of formula (V).

A variety of oxidizing agents are known to be useful for the conversion of primary alcohols to aldehydes. For example, a solution of the alcohol in a suitable solvent such as dichloromethane may be treated with Dess-Martin reagent (1,1,1-triacetoxy-1,1-dihydro-1,2-benziodoxol-3 (1H)-one). The reaction mixture is generally stirred until the reaction is judged to be complete and the product is isolated using standard methods.

In process step (d), the 4-aryl-3,6-dichloro-pyridazine-5-carbaldehyde of formula (V) is reacted with a hydrazine derivative of formula (VI) to provide a 4-aryl-5-chloropyrazolo[3,4-c]pyridazine of formula (VII). The hydrazine derivative may be generated in situ from a suitable salt, such as the oxalate, by treatment with a base such as triethylamine. The components are heated together in a suitable solvent, such as ethanol, until the reaction is judged to be complete and the product is isolated using standard methods.

In process step (e), the 4-aryl-5-chloropyrazolo[3,4-c]pyridazine of formula (VII) is coupled with an arylboronic acid derivative of formula (VIII) to provide a 4-(biphenyl-3-yl)-5-chloropyrazolo[3,4-c]pyridazine of formula (IX). The boronic acid derivative may be in the form of the free boronic acid (R=H) or a di-ester thereof, such as the cyclic di-ester formed with 2,3-dimethylbutane-2,3-diol

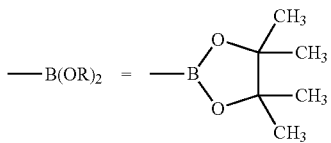

The pyrazolopyridazine and the aryl boronic acid derivative are combined in a suitable solvent in the presence of a palladium catalyst and a base. Suitable solvents may include dimethylformamide and mixtures of water and dioxin. The palladium catalyst may be pre-formed, such as tetrakis(triphenylphosphine)palladium(0) or it may be formed in situ, for example from tris(dibenzylideneacetone)dipalladium(0) and tri(tert-butyl)phosphine. Suitable bases may include sodium carbonate and cesium fluoride. The components are heated together until the reaction is judged to be complete and the product is isolated using standard methods.

In process step (f), the 4-(biphenyl-3-yl)-5-chloropyrazolo[3,4-c]pyridazine of formula (IX) is reductively dechlorinated to provide a 4-(biphenyl-3-yl)pyrazolo[3,4-c]pyridazine of formula (I). The reaction is typically accomplished by hydrogenation of a solution of the chloropyrazolopyridazine in a suitable solvent, such as methanol, ethanol, ethyl acetate and mixtures thereof, in the presence of a suitable catalyst, such as palladium-on-carbon, It may conveniently be carried out in a continuous flow device. Hydrogenation is continued until the reaction is judged to be complete and the product is isolated using standard methods.

3,6-Dichloropyridazine, 4-substituted-3-bromoiodobenzenes of formula (II), hydrazine derivatives of formula (VI and, arylboronic acid derivatives of formula (VIII) are available commercially and/or may be prepared by methods described in the literature.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 μg to 100 mg of the compound of formula (I). The overall daily dose will typically be in the range 1 μg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 0.1 mg to 10 g, such as 1 mg to 1 g, for example 2.5 mg to 500 mg depending, of course, on the mode of administration and efficacy.

For example, oral administration may require a total daily dose of from 5 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

The compounds of the invention are useful because they exhibit pharmacological activity, i.e., $GABA_A$ channel modulation. More particularly, the compounds of the invention are positive allosteric modulators of the $GABA_A$ channel. Preferred compounds of the invention are selective modulators of the $\alpha_2$, $\alpha_3$ and/or $\alpha_5$ subtypes, with lower efficacy and/or affinity at the $\alpha_1$, $\alpha_4$ and/or $\alpha_6$ subtypes. The compounds of the invention are accordingly of use in the treatment of disorders in animals for which a $GABA_A$ positive allosteric modulator is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a $GABA_A$ positive allosteric modulator is indicated.

In a further aspect of the invention there is provided use of a compound of the invention for the preparation of a medicament for the treatment of a disorder for which a $GABA_A$ positive allosteric modulator is indicated.

In a further aspect of the invention there is provided a method of treating a disorder in an animal (preferably a mammal, more preferably a human) for which a $GABA_A$ positive allosteric modulator is indicated, comprising administering to said animal a therapeutically effective amount of a compound of the invention.

The $GABA_A$ positive allosteric modulators of formula (I) may be effective in treating conditions wherein CNS hyperexcitability leads to dysfunction.

The $GABA_A$ positive allosteric modulators of formula (I) may be used:

- as analgesics, for example for the treatment of pain, including acute pain, chronic pain, neuropathic pain, nociceptive (including inflammatory) pain, somatic pain, visceral pain, and dysfunctional pain, as further discussed below, and in particular for pain conditions wherein there is a brain or spinal component to the underlying mechanism;
- as anticonvulsants, for example for the treatment of epilepsy and epilepsy associated disorders, including Lennox-Gastaut syndrome, Dravet's disease, and generalised epilepsy with febrile seizures plus (GEFS+);
- as anxiolytic agents, for example for the treatment of panic disorder, generalized anxiety disorder, stress disorders such as post-traumatic stress disorder, acute stress disorder and substance-induced stress disorder, phobias such as agoraphobia, social phobia and animal phobias, and obsessive-compulsive disorder; and
- as muscle relaxants, for example for the treatment of muscle spasm, dystonia, spasticity (including generalised and focal spasticity) and essential tremor.

The $GABA_A$ positive allosteric modulators of formula (I) may also be used for the treatment of autism, or as antipsychotic agents, for example for the treatment of schizophrenia.

Other therapeutic indications for the $GABA_A$ positive allosteric modulators of formula (I) include use as antidepressant agents, for example for the treatment of depressive and bipolar disorders and cyclothymia; as antiemetic agents, for example for the treatment of chemotherapy- or radiation-induced emesis, post-operative nausea and vomiting, and motion sickness; as cognition-enhancing agents, for example for the treatment of neurodegenerative disorders, such as Alzheimer's disease, and cerebral ischemia; as sleep improving agents, for example for the treatment of sleep disorders such as insomnia and circadian rhythm disorders such as jet-lag, or for use as pre-medication prior to anaesthesia or endoscopy; and use in the treatment of addiction phenotypes such as alcoholism, Angelman syndrome, attention deficit hyperactivity disorder, bladder urgency, bowel abnormalities, eating disorders such as anorexia nervosa and bulimia nervosa, Fragile X syndrome, hearing disorders such as tinnitus and age-related hearing impairment, multiple sclerosis, neuroses, overactive bladder with sensory disturbance, premenstrual syndrome, restless legs syndrome, and urinary incontinence.

A preferred use for the compounds of formula (I) is the treatment of pain. Pain may be either acute or chronic and additionally may be of central and/or peripheral origin. Pain may be of a neuropathic and/or nociceptive and/or inflammatory nature, such as pain affecting either the somatic or visceral systems, as well as dysfunctional pain affecting multiple systems.

Physiological pain is an important protective mechanism designed to warn of danger from potentially injurious stimuli from the external environment. The system operates through a specific set of primary sensory neurones and is activated by noxious stimuli via peripheral transducing mechanisms (see Meyer et al., 2006, Wall and Melzack's Textbook of Pain ($5^{th}$ Ed), Chapter 1). These sensory fibres are known as nociceptors, and are characteristically small diameter axons with slow conduction velocities, of which there are two main types, A-delta fibres (myelinated) and C fibres (non-myelinated). Nociceptors encode the intensity, duration and quality of noxious stimulus and by virtue of their topographically organised projection to the spinal cord, the location of the stimulus. The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually, although not always, associated with a specific cause such as a defined injury, is often sharp and severe and can result from numerous origins such as surgery, dental work, a strain or a sprain. Acute pain does not generally result in any persistent psychological response. When a substantial injury occurs to body tissue, via disease or trauma, the characteristics of nociceptor activation may be altered such that there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury or alteration which can be associated with maladaptation and aberrant activity (Woolf & Salter, 2000, Science, 288, 1765-1768). As such, chronic pain is long-term pain, typically persisting for more than three months and leading to significant psychological and emotional problems. Common examples of chronic pain are neuropathic pain (e.g. painful diabetic neuropathy or postherpetic neuralgia), carpal tunnel syndrome, back pain, headache, cancer pain, arthritic pain and chronic post-surgical pain, but may include any chronic painful condition affecting any system, such as those described by the International Association for the Study of Pain (Classification of Chronic Pain, a publication freely available for download at http://www.iasp-pain.org).

The clinical manifestation of pain is present when discomfort and abnormal sensitivity feature among the patient's symptoms. Patients tend to be quite heterogeneous and may present with various pain symptoms. Such symptoms can include: 1) spontaneous pain which may be dull, burning, or stabbing; 2) exaggerated pain responses to noxious stimuli (hyperalgesia); and 3) pain produced by normally innocuous stimuli (allodynia) (Meyer et al., 2006, Wall and Melzack's Textbook of Pain ($5^{th}$ Ed), Chapter 1). Although patients suffering from various forms of acute and chronic pain may have similar symptoms, the underlying mechanisms may be different and may, therefore, require different treatment strategies. Apart from acute or chronic, pain can also be broadly categorized into: nociceptive pain, affecting either the somatic or visceral systems, which can be inflammatory in nature (associated with tissue damage and the infiltration of immune cells); or neuropathic pain.

Nociceptive pain can be defined as the process by which intense thermal, mechanical, or chemical stimuli are detected by a subpopulation of peripheral nerve fibers, called nociceptors, and can be induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 2006, Wall and Melzack's Textbook of Pain ($5^{th}$ Ed), Chapter 1). Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from strains/sprains, burns, myocardial infarction and acute pancreatitis, post-operative pain (pain following any type of surgical procedure), posttraumatic pain, pain associated with gout, cancer pain and back pain. Cancer pain may be chronic pain such as tumour related pain (e.g. bone pain, headache, facial pain or visceral pain) or pain associated with cancer therapy (e.g. in response to chemotherapy, immunotherapy, hormonal therapy or radiotherapy). Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Nociceptive pain can also be related to inflammatory states. The inflammatory process is a complex series of biochemical and cellular events, activated in response to tissue injury or the presence of foreign substances, which results in swelling and pain (McMahon et al., 2006, Wall and Melzack's Textbook of Pain ($5^{th}$ Ed), Chapter 3). A common inflammatory condition associated with pain is arthritis. It has been estimated that almost 27 million Americans have symptomatic osteoarthritis (OA) or degenerative joint disease (Lawrence et al., 2008, Arthritis Rheum, 58, 15-35); most patients with osteoarthritis seek medical attention because of the associated pain. Arthritis has a significant impact on psychosocial and physical function and is known to be the leading cause of disability in later life. Rheumatoid arthritis is an immune-mediated, chronic, inflammatory polyarthritis disease, mainly affecting peripheral synovial joints. It is one of the commonest chronic inflammatory conditions in developed countries and is a major cause of pain.

In regard to nociceptive pain of visceral origin, visceral pain results from the activation of nociceptors of the thoracic, pelvic, or abdominal organs (Bielefeldt and Gebhart, 2006, Wall and Melzack's Textbook of Pain ($5^{th}$ Ed), Chapter 48). This includes the reproductive organs, spleen, liver, gastrointestinal and urinary tracts, airway structures, cardiovascular system and other organs contained within the abdominal cavity. As such visceral pain refers to pain associated with conditions of such organs, such as painful bladder syndrome, interstitial cystitis, prostatitis, ulcerative colitis, Crohn's disease, renal colic, irritable bowl syndrome, endometriosis and dysmenorrheal (Classification of Chronic Pain, available at http://www.iasp-pain.org). Currently the potential for a neuropathic contribution (either through central changes or nerve injury/damage) to visceral pain states is poorly understood but may play a role in certain conditions (Aziz et al., 2009, Dig Dis 27, Suppl 1, 31-41)

Neuropathic pain is currently defined as pain arising as a direct consequence of a lesion or disease affecting the somatosensory system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Dworkin, 2009, Am J Med, 122, S1-S2; Geber et al., 2009, Am J Med, 122, S3-S12; Haanpaa et al., 2009, Am J Med, 122, S13-S21). The symptoms of neuropathic pain are difficult to treat, as they are often heterogeneous even between patients with the same disease (Dworkin, 2009, Am J Med, 122, S1-S2; Geber et al., 2009, Am J Med, 122, S3-S12; Haanpaa et al., 2009, Am J Med, 122, S13-S21). They include spontaneous pain, which can be continuous, and paroxysmal or abnormal evoked pain, such as hyperalgesia (increased sensitivity to a noxious stimulus) and allodynia (sensitivity to a normally innocuous stimulus).

It should be noted that some types of pain have multiple aetiologies and thus can be classified in more than one area, e.g. back pain, cancer pain and even migraine headaches may include both nociceptive and neuropathic components.

Similarly other types of chronic pain, perhaps less well understood, are not easily defined by the simplistic definitions of nociceptive or neuropathic. Such conditions include in particular fibromyalgia and chronic regional pain syndrome, which are often described as dysfunctional pain states e.g. fibromyalgia or complex regional pain syndrome (Woolf, 2010, J Clin Invest, 120, 3742-3744), but which are included in classifications of chronic pain states (Classification of Chronic Pain, available at http://www.iasp-pain.org).

A $GABA_A$ positive allosteric modulator may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

For the treatment of pain, a $GABA_A$ positive allosteric modulator of formula (I), or a pharmaceutically acceptable salt thereof, as defined above, may be administered in combination with one or more agents selected from:

a selective Nav1.3 channel modulator, such as a compound disclosed in WO2008/118758;

a selective Nav1.7 channel modulator, such as a compound disclosed in WO2010/079443, e.g. 4-[2-(5-amino-1H-pyrazol-4-yl)-4-chlorophenoxy]-5-chloro-2-fluoro-N-1,3-thiazol-4-ylbenzenesulfonamide or 4-[2-(3-amino-1H-pyrazol-4-yl)-4-(trifluoromethyl) phenoxy]-5-chloro-2-fluoro-N-1,3-thiazol-4-ylbenzenesulfonamide, or a pharmaceutically acceptable salt of either;

a selective Nav1.8 channel modulator;

a selective Nav1.9 channel modulator;

a compound which modulates activity at more than one Nav channel, including a non-selective modulator such as bupivacaine, carbamazepine, lamotrigine, lidocaine, mexiletine or phenytoin;

any inhibitor of nerve growth factor (NGF) signaling, such as: an agent that binds to NGF and inhibits NGF biological activity and/or downstream pathway(s) mediated by NGF signaling (e.g. tanezumab), a TrkA antagonist or a p75 antagonist, or an agent that inhibits downstream signaling in regard to NGF stimulated TrkA or P75 signalling;

an inhibitor of neurotrophic pathways, where such inhibition is achieved by: (a) an agent that binds to nerve growth factor (NGF) (e.g. tanezumab, fasinumab or fulranumab), brain-derived neurotrophic factor (BDNF), neurotrophin-3 (NT-3) or neurotrophin-4 (NT-4), or to more than one of the aforementioned neurotrophins (e.g. soluble P75); or (b) an agent that inhibits receptor function at one or more of TrKA, TrKB, TrKC or P75, either at the orthosteric site, an allosteric site or by inhibition of the catalytic activity of the receptor(s);

a compound which increases the levels of endocannabinoid, such as a compound with fatty acid amid hydrolase inhibitory (FAAH) or monoacylglycerol lipase (MAGL) activity;

an analgesic, in particular paracetamol;

an opioid analgesic, such as: buprenorphine, butorphanol, cocaine, codeine, dihydrocodeine, fentanyl, heroin, hydrocodone, hydromorphone, levallorphan levorphanol, meperidine, methadone, morphine, nalmefene, nalorphine, naloxone, naltrexone, nalbuphine, oxycodone, oxymorphone, propoxyphene or pentazocine;

an opioid analgesic which preferentially stimulates a specific intracellular pathway, for example G-protein as opposed to beta arrestin recruitment, such as TRV130;

an opioid analgesic with additional pharmacology, such as: noradrenaline (norepinephrine) reuptake inhibitory (NRI) activity, e.g. tapentadol; serotonin and norepinephrine reuptake inhibitory (SNRI) activity, e.g. tramadol; or nociceptin receptor (NOP) agonist activity, such as GRT6005;

a nonsteroidal antiinflammatory drug (NSAID), such as a non-selective cyclooxygenase (COX) inhibitor, e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac; or a COX-2 selective inhibitor, e.g. celecoxib, deracoxib, etoricoxib, mavacoxib or parecoxib;

a prostaglandin E2 subtype 4 (EP4) antagonist;

a microsomal prostaglandin E synthase type 1 (mPGES-1) inhibitor;

a sedative, such as glutethimide, meprobamate, methaqualone or dichloralphenazone;

a GABA$_A$ modulator with broad subtype modulatory effects mediated via the benzodiazepine binding site, such as chlordiazepoxide, alprazolam, diazepam, lorazepam, oxazepam, temazepam, triazolam, clonazepam or clobazam;

a GABA$_A$ modulator with subtype-selective modulatory effects mediated via the benzodiazepine binding site with reduced adverse effects, for example sedation, such as TPA023, TPA023B, L-838,417, CTP354 or NSD72;

a GABA$_A$ modulator acting via alternative binding sites on the receptor, such as barbiturates, e.g. amobarbital, aprobarbital, butabital, mephobarbital, methohexital, pentobarbital, phenobartital, secobarbital, or thiopental; neurosteroids such as alphaxalone, alphadolone or ganaxolone; β-subunit ligands, such as etifoxine; or δ-preferring ligands, such as gaboxadol;

a GlyR3 agonist or positive allosteric modulator;

a skeletal muscle relaxant, e.g. baclofen, carisoprodol, chlorzoxazone, cyclobenzaprine, metaxolone, methocarbamol or orphrenadine;

a glutamate receptor antagonist or negative allosteric modulator, such as an NMDA receptor antagonist, e.g. dextromethorphan, dextrorphan, ketamine or, memantine; or an mGluR antagonist or modulator;

an alpha-adrenergic, such as clonidine, guanfacine or dexmetatomidine;

a beta-adrenergic such as propranolol;

a tricyclic antidepressant, e.g. desipramine, imipramine, amitriptyline or nortriptyline;

a tachykinin (NK) antagonist, such as aprepitant or maropitant;

a muscarinic antagonist, e.g oxybutynin, tolterodine, propiverine, tropsium chloride, darifenacin, solifenacin, temiverine and ipratropium;

a cholinergic (nicotinic) analgesic, such as ispronicline (TC-1734), varenicline or nicotine;

a Transient Receptor Potential V1 (TRPV1) receptor agonist (e.g. resinferatoxin or capsaicin) or antagonist (e.g. capsazepine or mavatrap);

a Transient Receptor Potential A1 (TRPA1) receptor agonist (e.g. cinnamaldehyde or mustard oil) or antagonist (e.g. GRC17536 or CB-625);

a Transient Receptor Potential M8 (TRPM8) receptor agonist (e.g. menthol or icilin) or antagonist;

a Transient Receptor Potential V3 (TRPV3) receptor agonist or antagonist (e.g. GRC-15300);

a corticosteroid such as dexamethasone;

a 5-HT receptor agonist or antagonist, particularly a 5-HT$_{1B/1D}$ agonist, such as eletriptan, sumatriptan, naratriptan, zolmitriptan or rizatriptan;

a 5-HT$_{2A}$ receptor antagonist;

a PDEV inhibitor, such sildenafil, tadalafil or vardenafil;

an alpha-2-delta ligand such as gabapentin, gabapentin enacarbil or pregabalin;

a serotonin reuptake inhibitor (SRI) such as sertraline, demethylsertraline, fluoxetine, norfluoxetine, fluvoxamine, paroxetine, citalopram, desmethylcitalopram, escitalopram, d,l-fenfluramine, femoxetine, ifoxetine, cyanodothiepin, litoxetine, dapoxetine, nefazodone, cericlamine and trazodone;

an NRI, such as maprotiline, lofepramine, mirtazepine, oxaprotiline, fezolamine, tomoxetine, mianserin, buprorion, buprorion metabolite hydroxybuproprion, nomifensine and viloxazine, especially a selective noradrenaline reuptake inhibitor such as reboxetine;

an SNRI, such as venlafaxine, O-desmethylvenlafaxine, clomipramine, desmethylclomipramine, duloxetine, milnacipran and imipramine;

an inducible nitric oxide synthase (iNOS) inhibitor;

a leukotriene B4 antagonist;

a 5-lipoxygenase inhibitor, such as zileuton;

a potassium channel opener or positive modulator, such as an opener or positive modulator of KCNQ/Kv7 (e.g. retigabine or flupirtine), a G protein-coupled inwardly-rectifying potassium channel (GIRK), a calcium-activated potassium channel (Kca) or a potassium voltage-gated channel such as a member of subfamily A (e.g. Kv1.1), subfamily B (e.g. Kv2.2) or subfamily K (e.g. TASK, TREK or TRESK);

a P2X$_3$ receptor antagonist (e.g. AF219) or an antagonist of a receptor which contains as one of its subunits the P2X$_3$ subunit, such as a P2X$_{2/3}$ heteromeric receptor;

a Ca$_V$2.2 calcium channel blocker (N-type), such as ziconotide; and a Ca$_V$3.2 calcium channel blocker (T-type), such as ethosuximide.

For the treatment of epilepsy, a GABA$_A$ positive allosteric modulator of formula (I), or a pharmaceutically acceptable salt thereof, as defined above, may be administered in combination with one or more agents selected from:

an acetylurea such as phenacemide or pheneturide;

an alpha-2-delta ligand such as gabapentin or pregabalin;

a barbiturate such as barbexaclone, eterobarb, mephobarbital, metharbital or phenobarbital, or a deoxybarbiturate such as primidone;

a benzodiazepine such as clobazam, clonazepam or nitrazepam;

a gamma-aminobutyric acid (GABA) analog such as 4-amino-3-hydroxybutyric acid, progabide, tiagabine or vigabatrin;

an iminostilbene such as carbamazepine, eslicarbazepine acetate or oxcarbazepine;

a hydantoin such as ethotoin, mephenytoin, phenytoin or phenytoin sodium;

an oxazolidinedione such as ethadione, paramethadione, troxidone a succinimide such as ethosuximide, mesuximide or phensuximide a valproate such as valproate sodium, valproic acid or valpromide;

acetazolamide; beclamide, felbamate, lacosamide, lamotrigine, levetiracetam, milacemide, nafimidone, perampanel, piracetam, retigabine, rufinamide, stiripentol, sulthiame, topiramate or zonisamide There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450

(CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl)acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a GABA-A modulator is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:

br is broad;
° C. is degrees Celcius
$CDCl_3$ is deutero-chloroform;
$CD_3OD$ is perdeuteromethanol:
δ is chemical shift;
d is doublet;
DCM is dichloromethane; methylene chloride;
dd is double-doublet;
ddd is double-double-doublet;
DMF is N,N-dimethylformamide;
DMSO-$d_6$ is perdeutero-dimethyl sulphoxide;
ELSD is evaporative light scattering detection;
EtOAc is ethyl acetate;
EtOH is ethanol;
g is gram;
HPLC is high pressure liquid chromatography;
L is litre;
LCMS is liquid chromatography mass spectrometry (Rt=retention time);
m is multiplet;
M is molar;
MeCN is acetonitrile;
MeOH is methanol;
mg is milligram;
MHz is megaHertz;
min is minutes;
mL is milli litre;
mmol is millimole;
mol is mole;
MS m/z is mass spectrum peak;
$NaHCO_3$ is sodium hydrogencarbonate;
$Na_2CO_3$ is sodium carbonate;
NMR is nuclear magnetic resonance;
P(2-furyl)$_3$ is tris(2-furyl)phosphine
Pd(dba)$_2$ is bis(dibenzylideneacetone)palladium(0);
Pd$_2$(dba)$_3$ is tris(dibenzylideneacetone)dipalladium(0);
Pd(PPh$_3$)$_4$ is tetrakis(triphenylphosphine)palladium(0);
pH is power of hydrogen;
ppm is parts per million;
q is quartet;
s is singlet;
t is triplet;
TEA is trimethylamine;
THF is tetrahydrofuran;
TLC is thin layer chromatography;
μL is microlitre; and
μmol is micromol The Preparations and Examples that follow illustrate the invention but do not limit the invention in any way. All starting materials are available commercially or described in the literature. All temperatures are in ° C. Silica gel column chromatography was carried out using Merck silica gel 60 (9385). Thin layer chromatography (TLC) was carried out on Merck silica gel 60 plates (5729). $^1$H- and $^{19}$F-NMR spectra were recorded on a Varian Mercury 300 or 400 MHz, Bruker Avance 400 MHz NMR or Jeol ECX 400 MHz. When peak multiplicities are reported, the following abbreviations are used: s=singlet, d=doublet, t=triplet, m=multiplet, br=broadened, dd=doublet of doublets, dt=doublet of triplets.

LCMS indicates liquid chromatography mass spectrometry ($R_t$=retention time). Where ratios of solvents are given, the ratios are by volume.

Mass spectra (MS) were recorded using either electrospray ionisation (ESI) or atmospheric pressure chemical ionisation (APCI). Mass spectroscopy was carried out using a Finnigan Navigator single quadrupole electrospray mass spectrometer, Finnigan aQa APCI mass spectrometer or Applied Biosystem Q-Trap Where it is stated that compounds were prepared in the manner described for an earlier Preparation or Example, the skilled person will appreciate that reaction times, number of equivalents of reagents and reaction temperatures may have been modified for each specific reaction, and that it may nevertheless be necessary, or desirable, to employ different work-up or purification conditions.

Preparation 1

4-(3-Bromo-4-fluorophenyl)-3,6-dichloropyridazine

A solution of commercially-prepared 2,2,6,6-bis(tetramethylpiperidine)zinc lithium chloride complex (0.35 M, 41 mL, 14.3 mmol) was treated with a solution of 3,6-dichloropyridazine (2 g, 13 mmol) in THF (24 mL) slowly, and the mixture was stirred at room temperature for 30 minutes. A solution of Pd(dba)$_2$ (225 mg, 0.39 mmol), P(2-furyl)$_3$ (181 mg, 0.78 mmol), and 3-bromo-4-fluoroiodobenzene (5.1 g, 16.9 mmol) in THF (24 mL) was added, and the resulting mixture was stirred at room temperature for 3 hours. The reaction mixture was quenched with saturated ammonium chloride, diluted with water, and extracted with EtOAc (2×). The combined organics were dried over magnesium sulfate, filtered and concentrated under reduced pressure to afford 8.9 g of a light-brown solid. The crude was slurried in methanol (10 mL) for 1 hour, then filtered to provide the title compound as a beige solid (1.61 g, 38%).

LCMS: AP$^+$ (M+H)$^+$ 321.0/323.0 (100% ELSD) R$_t$=0.94 min (1.5 min run-time)

$^1$H NMR (500 MHz, CD$_3$OD) δ 7.90-7.97 (m, 2H) 7.63 (ddd, J=8.54, 4.51, 2.32 Hz, 1H) 7.41 (t, J=8.54 Hz, 1H) ppm Preparation 2

[5-(3-Bromo-4-fluorophenyl)-3,6-dichloropyridazin-4-yl]methanol

A solution of 4-(3-bromo-4-fluoro-phenyl)-3,6-dichloro-pyridazine (Preparation 1, 1 g, 3.1 mmol) in DCM (75 mL) and MeOH (125 mL) was treated with a solution of iron(II) sulfate (1.2 g, 12.5 mmol) in water (2.5 mL), followed by concentrated sulfuric acid (0.75 mL, 14 mmol). The mixture was heated to reflux and was then treated drop-wise with aqueous hydrogen peroxide (30%, 5.0 mL, 49.3 mmol). The mixture was treated with another 5 mL of oxidant after 2, 4, 22, and 27 hours. After 30 hours total, upon consumption of starting material, the mixture was cooled to room temperature and treated carefully with saturated aqueous potassium carbonate until bubbling stopped. The mixture was concentrated under reduced pressure to remove the organic solvents and extracted into DCM (3 times). The combined organics were dried over magnesium sulfate, filtered and concentrated under reduced pressure to afford 1.16 g of a light-brown oil, which was purified using medium-pressure chromatography (24 g silica, 0-30% EtOAc/heptane, 12 column volumes). Product fractions were concentrated under reduced pressure to afford the title compound as a colorless foam (426 mg, 39%).

LCMS: ES+ (M+H)+351.0/353.0, R$_t$=0.81 min (1.5 min run-time)

$^1$H NMR (500 MHz, CDCl$_3$) δ 7.59 (dd, J=6.22, 2.07 Hz, 1H) 7.23-7.39 (m, 2H) 4.56 (m, 2H) 3.24 (br. s., 1H) ppm Preparation 3

5-(3-Bromo-4-fluorophenyl)-3,6-dichloropyridazine-4-carbaldehyde

A solution of [5-(3-bromo-4-fluorophenyl)-3,6-dichloro-pyridazin-4-yl]-methanol (Preparation 2, 238 mg, 0.68 mmol) in DCM (10 mL) was treated with Dess-Martin reagent (332 mg, 0.74 mmol) and stirred at room temperature for 1 hour. The reaction mixture was quenched with saturated aqueous NaHCO$_3$ and saturated aqueous sodium thiosulfate (6 mL each) and was stirred for 30 minutes. The layers were separated and the aqueous was extracted twice more with DCM. The combined organics were dried over magnesium sulfate, filtered and concentrated under reduced pressure to afford 208 mg of a yellow oil. The crude material was purified using medium pressure chromatography (12 g silica, 0-30% EtOAc/heptane, 24 column volumes). Product fractions were combined and concentrated under reduced pressure to afford the title compound as a yellow film (150 mg, 63%).

LCMS: AP$^+$ (M+H)$^+$ 349.0/351.0, R$_t$=0.86/0.91 min (1.5 min run-time)

$^1$H NMR (500 MHz, CDCl$_3$) δ 10.07 (s, 1H) 7.52 (dd, J=6.34, 2.20 Hz, 1H) 7.26-7.33 (m, 1H) 7.21-7.26 (m, 1H) ppm Preparation 4

4-(3-Bromo-4-fluorophenyl)-5-chloro-1-ethyl-1H-pyrazolo[3,4-c]pyridazine

A solution of 5-(3-bromo-4-fluoro-phenyl)-3,6-dimethoxy-pyridazine-4-carbaldehyde (Preparation 3, 150 mg, 0.43 mmol), ethylhydrazine oxalate (71 mg, 0.47 mmol) and TEA (0.2 mL, 1.4 mmol) in EtOH (5 mL) was stirred at room temperature for 1 h and then heated to 120° C. for 10 minutes on the microwave. The crude was purified using medium-pressure chromatography (12 g silica, 0-25% EtOAc/heptane, 25 column volumes). Product fractions were combined and concentrated under reduced pressure to afford the title compound as a yellow solid (84 mg, 55% yield).

LCMS: ES$^+$ (M+H)$^+$ 357.0 (100% ELSD) 0.98 min (1.5 min run-time)

$^1$H NMR (500 MHz, CDCl$_3$) δ 7.96 (s, 1H) 7.87 (dd, J=6.34, 2.20 Hz, 1H) 7.60 (ddd, J=8.48, 4.57, 2.32 Hz, 1H) 7.35 (t, J=8.29 Hz, 1H) 4.82 (q, J=7.16 Hz, 2H) 1.65 (t, J=7.20 Hz, 3H) ppm Preparation 5

5-Chloro-4-(4'-ethanesulfonyl-6-fluoro-2'-methoxy-biphenyl-3-yl)-1-ethyl-1H-pyrazolo[3,4-c]pyridazine A solution of 2-(4-ethanesulfonyl-2-methoxy-phenyl)-4,4,5,5-tetramethyl-[1,3,2]dioxaborolane (44 mg, 0.14 mmol), 4-(3-bromo-4-fluoro-phenyl)-5-chloro-1-ethyl-1H-pyrazolo[3,4-c]pyridazine (Preparation 4, 44 mg, 0.12 mmol), and Na$_2$CO$_3$ (40 mg, 0.37 mmol) in dioxane (4 mL) and water (1 mL) was degassed with nitrogen, treated with Pd(PPh$_3$)$_4$ (15 mg, 0.012 mmol) and heated to reflux for 15 hours. The mixture was cooled to room temperature and concentrated under reduced pressure to afford 184 mg of a brown oil, which was purified using medium-pressure chromatography (12 g silica, 0-40% EtOAc/heptane, 25 column volumes). Product fractions were combined and concentrated under reduced pressure to afford the title compound as a colorless solid (39 mg, 66%).

LCMS: ES$^+$ (M+H)$^+$ 475.2, R$_t$=0.92 min (1.5 min run-time)

$^1$H NMR (500 MHz, CDCl$_3$) δ 8.02 (s, 1H) 7.69-7.76 (m, 2H) 7.58-7.63 (m, 1H) 7.54-7.58 (m, 1H) 7.53 (d, J=1.71 Hz, 1H) 7.35-7.42 (m, 1H) 4.81 (q, J=7.32 Hz, 2H) 3.95 (s, 3H) 3.19 (q, J=7.32 Hz, 2H) 1.64 (t, J=7.20 Hz, 3H) 1.36 (t, J=7.44 Hz, 3H) ppm Preparation 6

5-Chloro-4-(4'-ethanesulfonyl-6-fluorobiphenyl-3-yl)-1-ethyl-1H-pyrazolo[3,4-c]pyridazine A solution of 4-(ethylsulfonyl)benzeneboronic acid (29 mg, 0.14 mmol), 4-(3-bromo-4-fluoro-phenyl)-5-chloro-1-ethyl-1H-pyrazolo[3,4-c]pyridazine (Preparation 4, 43 mg, 0.12 mmol), and Na$_2$CO$_3$ (40 mg, 0.37 mmol) in dioxane (4 mL) and water (1 mL) was degassed with nitrogen, treated with Pd(PPh$_3$)$_4$ (15 mg, 0.012 mmol) and heated to reflux for 15 hours. The mixture was cooled to room temperature and concentrated under reduced pressure to afford a yellow oil, which was purified using medium-pressure chromatography (12 g silica, 0-40% EtOAc/heptane, 20 column volumes).

Product fractions were combined and concentrated under reduced pressure to afford the title compound as a colorless solid (40 mg, 74%).

LCMS: ES+ (M+H)+ 445.2 (100% ELSD), R$_t$=0.92 min (1.5 min run-time)

$^1$H NMR (500 MHz, CDCl$_3$) δ 8.03 (d, J=8.54 Hz, 2H) 7.99 (s, 1H) 7.81 (dd, J=8.54, 1.46 Hz, 2H) 7.78 (dd, J=7.20, 2.32 Hz, 1H) 7.71 (ddd, J=8.48, 4.57, 2.32 Hz, 1H) 7.44 (dd, J=10.00, 8.54 Hz, 1H) 4.82 (q, J=7.16 Hz, 2H) 3.18 (q, J=7.40 Hz, 2H) 1.61-1.68 (m, 3H) 1.34 (t, J=7.44 Hz, 3H) ppm Preparation 7

5-[5-(5-Chloro-1-ethyl-1H-pyrazolo[3,4-c]pyridazin-4-yl)-2-fluorophenyl]-6-methoxy-2-methyl-2,3-dihydroisoindol-1-one A solution of 6-methoxy-2-methyl-2,3-dihydroisoindol-1-on5-ylboronic acid (37 mg, 0.17 mmol), 4-(3-bromo-4-fluoro-phenyl)-5-chloro-1-ethyl-1H-pyrazolo[3,4-c]pyridazine (Preparation 4, 50 mg, 0.14 mmol), Pd$_2$(dba)$_3$ (6.4 mg, 0.007 mmol), tri(tert-butyl)phosphine tetrafluoroborate (8.2 mg, 0.028 mmol) and freshly ground cesium fluoride (85 mg, 0.56 mmol) in degassed DMF (1.4 mL) was stirred at room temperature for 24 h under nitrogen in a sealed vial, then heated at 50° C. for 6 h, then at 80° C. for 18 h, and finally at 110° C. for 24 h, then allowed to cool to room temperature and diluted with water. The solid material was collected by filtration and the filtrate was concentrated then filtered again. The combined solids were purified using column chromatography (EtOAc). Product fractions were combined and concentrated under reduced pressure to afford the title compound as a colorless solid (16 mg, 25%).

[M+H+]=452.1 (ES+)

1H NMR (600 MHz, CDCl$_3$) δ 8.03 (s, 1H), 7.73 (dd, J=6.8, 2.3 Hz, 1H), 7.70 (ddd, J=7.4, 4.5, 2.3 Hz, 1H), 7.48 (s, 1H), 7.42 (s, 1H), 7.37 (t, J=8.9 Hz, 1H), 4.81 (q, J=7.3 Hz, 2H), 4.38 (s, 2H), 3.93 (s, 3H), 3.23 (s, 3H), 1.64 (t, J=7.2 Hz, 3H) ppm Example 1

4-(4'-Ethanesulfonyl-6-fluoro-2'-methoxybiphenyl-3-yl)-1-ethyl-1H-pyrazolo[3,4-c]pyridazine

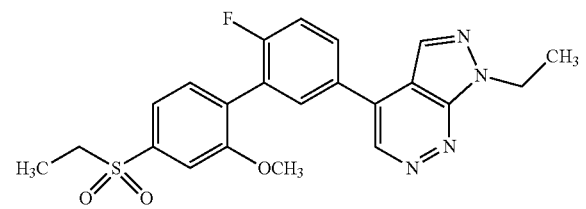 [SMILES: CCn1ncc2c(-c3ccc(F)c(-c4ccc(S(=O)(=O)CC)cc4OC)c3)cnnc21]

5 mg of 10% palladium on carbon was treated with a solution of 5-chloro-4-(4'-ethanesulfonyl-6-fluoro-2'-methoxy-biphenyl-3-yl)-1-ethyl-1H-pyrazolo[3,4-c]pyridazine (Preparation 5, 39 mg, 0.082 mmol) in EtOAc (10 mL) and EtOH (10 mL), and the mixture was pumped through an H-Cube device at 70° C., palladium on carbon cartridge, 1 mL/min, full H$_2$ (no pressure). The mixture was concentrated under reduced pressure to afford 37 mg of a greenish oil, which was purified using medium-pressure chromatography (12 g silica, 0-80% EtOAc/heptane, 28 column volumes). The product fractions were combined and concentrated to afford the title compound as a colorless solid (3.6 mg, 10%).

LCMS: ES+ (M+H)+ 441.3 (100% ELSD) R$_t$=0.85 min (1.5 min run-time)

$^1$H NMR (500 MHz, CDCl$_3$) δ ppm 9.25 (s, 1H) 8.29 (s, 1H) 7.82-7.91 (m, 2H) 7.60-7.66 (m, 1H) 7.53-7.59 (m, 2H) 7.38-7.46 (m, 1H) 4.87 (q, J=7.24 Hz, 2H) 3.96 (s, 3H) 3.21 (q, J=7.56 Hz, 2H) 1.66 (t, J=7.32 Hz, 3H) 1.38 (t, J=7.44 Hz, 3H) ppm Example 2

4-(4'-Ethanesulfonyl-6-fluorobiphenyl-3-yl)-1-ethyl-1H-pyrazolo[3,4-c]pyridazine

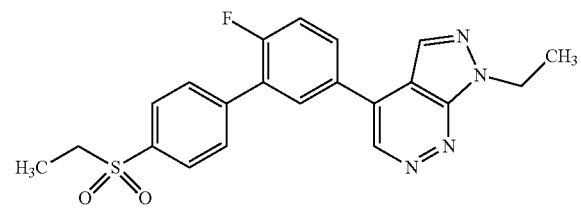 [SMILES: CCn1ncc2c(-c3ccc(F)c(-c4ccc(S(=O)(=O)CC)cc4)c3)cnnc21]

A solution of 5-chloro-4-(4'-ethanesulfonyl-6-fluoro-biphenyl-3-yl)-1-ethyl-1H-pyrazolo[3,4-c]pyridazine (Preparation 6, 40 mg, 0.09 mmol) in MeOH (30 mL) was passed through the H-Cube in a continuous loop at 70° C., palladium on carbon cartridge, 1 mL/min, full H$_2$ (no pressure). Total volume of 30 mL pumped at 1 mL/min for 4 hours=approximately 8 passes through the cartridge. The mixture was purified using medium-pressure chromatography (12 g silica, 0-65% EtOAc/heptane, 18 column volumes). The product fractions were combined and concentrated to afford the title compound as a colorless solid (3.5 mg, 10%).

LCMS: ES+ (M+H)+ 411.2 (100% ELSD) R$_t$=0.85 min (1.5 min run-time)

$^1$H NMR (500 MHz, CDCl$_3$) δ ppm 9.28 (s, 1H) 8.32 (s, 1H) 8.06 (d, J=8.54 Hz, 2H) 7.86-7.94 (m, 2H) 7.83 (dd, J=8.42, 1.34 Hz, 2H) 7.49 (dd, J=9.76, 8.54 Hz, 1H) 4.89 (q, J=7.32 Hz, 2H) 3.20 (q, J=7.32 Hz, 2H) 1.67 (t, J=7.32 Hz, 3H) 1.36 (t, J=7.44 Hz, 3H).

Example 3

5-[5-(1-Ethyl-1H-pyrazolo[3,4-c]pyridazin-4-yl)-2-fluorophenyl]-6-methoxy-2-methyl-2,3-dihydroisoindol-1-one

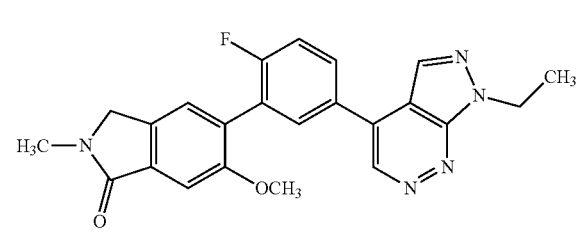 [SMILES: CCn1ncc2c(-c3ccc(F)c(-c4cc5c(cc4OC)C(=O)N(C)C5)c3)cnnc21]

A solution of 5-[5-(5-chloro-1-ethyl-1H-pyrazolo[3,4-c]pyridazin-4-yl)-2-fluorophenyl]-6-methoxy-2-methyl-2,3-dihydroisoindol-1-one (Preparation 7, 35 mg, 0.077 mmol) and TEA (39 mg, 0.39 mmol) in EtOH (77 mL) was hydrogenated over palladium on carbon in a high pressure flow reactor, then concentrated under reduced pressure. The residue was dissolved in ethyl acetate and filtered, then purified chromatography (EtOAc then EtOAc/EtOH 9/1). The product fractions were combined and concentrated to afford the title compound as a colorless solid (10 mg, 31%).

[M+H+]=418.8 (ES+)

1H NMR (600 MHz, DMSO-d$_6$) δ 9.47 (s, 1H), 8.66 (s, 1H), 8.14-8.07 (m, 1H), 8.06-7.99 (m, 1H), 7.68 (s, 1H), 7.56 (t, J=9.1 Hz, 1H), 7.38 (s, 1H), 4.77 (q, J=7.2 Hz, 2H), 4.46 (s, 2H), 3.87 (s, 3H), 3.11 (s, 3H), 1.54 (t, J=7.2 Hz, 3H).

Assay Methods

Cell Line Construction and Maintenance

Human Embryonic Kidney (HEK) cells were transfected with a GABRA2-GABRB2-GABRG2 construct using standard techniques. Cells stably expressing the GABRA2-GABRB2-GABRG2 constructs were identified by their resistance to Geneticin G-418 (320 µg/ml), Hygromycin (160 µg/ml) and Zeocin (40 µg/ml). Clones were screened for expression using the BD Pathway 855 imaging system (BD Biosciences, Rockville, Md., USA) and QPatch automated electrophysiology platform (Sophion, Copenhagen, Denmark).

Cell Culture

HEK cells stably transfected with GABRA2-GABRB2-GABRG2 were maintained in MEM medium with Earle's salts, 10% FBS, 1×L-Glutamax, 1% mM Non-essential Amino Acids (MEM) and 1 mM sodium pyruvate, with Geneticin G-418 (320 µg/ml), Hygromycin (160 µg/ml) and Zeocin (40 µg/ml), in an incubator at 37° C. with a humidified atmosphere of 5% $CO_2$. For QPatch electrophysiology testing, cells were harvested from flasks by enzymatic dissociation and resuspended in serum-free medium. Cells were typically used for electrophysiological experiments within 24 to 72 hours after splitting.

Binding Assay

The affinity of the test compounds was determined by radioligand competition binding assay, using the known compound [3H]Ro-15-1788 (Flumazenil) (Perkin Elmer, 85.4 Ci/mmol) and the human recombinant GABA A receptor containing the alpha2, beta2, and gamma2 subunits.

Membranes were prepared from HEK cells expressing hGABA A alpha2beta2-gamma2 receptor, and validated to ascertain protein concentration, receptor expression and to determine the Kd of the flumazenil as well as the Ki of a standard set of compounds before being used to test new compounds.

The assay was carried out in 96 well plates; testing compounds using a 10 point semi-log dilution range from 19 uM top concentration. 100 ul of radioligand and 100 ul of membrane in 50 mM Tris-HCl and 0.05% F127 with 1 ul of test compound was incubated for 2 hours to allow the reaction to achieve equilibrium, and then harvested onto filter plates, dried and counted on a TopCount NXT. The data was analysed, and the Ki values were presented as the geometric mean of at least two replicates.

Electrophysiological Recording

Cell suspension containing HEK cells expressing GABRA2-GABRB2-GABRG2 was placed on the QPatch instrument in serum-free medium into the instrument's cell stirrer. The instrument washed the cells once using extracellular buffer and then dispensed them into the QPlate HT measurement plate at a concentration of 3-4e6/ml. Extracellular solution was of the following composition: 137 mM NaCl, 1.8 mM $CaCl_2$, 4 mM KCl, 1 mM $MgCl_2$, 10 mM glucose, and 10 mM HEPES, pH 7.4 with NaOH, 300-310 mOsm/kg. The internal side of the QPlate measurement plate was filled with intracellular solution of the following composition: 90 mM KCl, 50 mM KF, 1 mM $MgCl_2$, 10 mM HEPES, 11 mM EGTA, and 2 mM Mg-ATP, pH 7.35, with KOH, 295-305 mOsm/kg. All recordings were made at room temperature (22-24° C.).

GABRA2-GABRB2-GABRG2 chloride currents in HEK cells were measured using the whole-cell configuration of the patch-clamp technique (Hamill et al., 1981). Current records were acquired at 1 KHz and filtered at 0.3 KHz using the Bessel filter. Series resistance compensation was set to 80% in the QPatch software.

All compounds were dissolved in dimethyl sulfoxide to make 30 mM or 10 mM stock solutions, which were then diluted to 1000 times the desired final concentration in dimethyl sulfoxide. These were diluted into extracellular solution to attain the final concentrations desired. The final concentration of dimethyl sulfoxide (<0.1% dimethyl sulfoxide) was found to have no significant effect on GABRA2-GABRB2-GABRG2 chloride currents. This concentration of dimethyl sulfoxide was present in all samples. Currents were recorded at −60 mV, using an approximately EC10 concentration of gamma-aminobutyric acid (GABA). This dose of gamma-aminobutyric acid was applied for 6 seconds and washed off using extracellular buffer as an unrecorded application using the pipetting system of the QPatch instrument. The same dose of gamma-aminobutyric acid was then applied for 9 seconds, then the test compound was co-applied with this dose of gamma-aminobutyric acid for 15 seconds, and washed off using the extracellular solution using the pipetting system of the QPatch instrument.

Compound effect (% enhancement of gamma-aminobutyric acid current) was calculated using the following formula:

[((peak modulator current amplitude-leak)−(GABA current amplitude-leak))/(GABA current amplitude-leak)]*100, where 'leak' is leak current at −60 mV, 'peak modulator current amplitude' is the current elicited by co-application of gamma-aminobutyric acid and test compound, and 'GABA current amplitude' is the current elicited by application of gamma-aminobutyric acid alone.

The ability of the compounds of the formula (I) to modulate the GABA channels expressing the α1 subunit (or GABRA1) can also be measured using an assay analogous to that described above but replacing the GABRA2-GABRB2-GABRG2 gene construct with the GABRA1-GABRB3-GABRG2 gene construct. All other conditions remain the same including the same cell line and conditions for cell growth. The % enhancement values generated in the assay using the GABRA1-GABRB3-GABRG2 construct can be compared to the results generated using the GABRA2-GABRB2-GABRG2 construct to determine the selectivity of a given compound.

Results

| Example | GABA-α2 Ki (nM) | α1 PAM (%) | α2 PAM (%) |
|---|---|---|---|
| 1 | <0.6 | 18 | 109 |
| 2 | 17.5 | 52 | 109 |
| 3 | 11.8 | ND | ND |

The invention claimed is:

1. A compound according to formula (I)

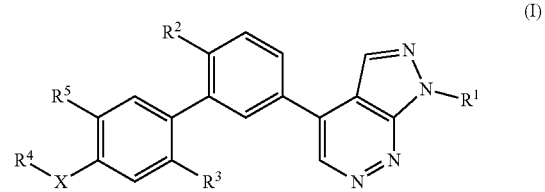

or a pharmaceutically acceptable salt thereof, wherein

X is selected from —S(O)$_2$— and —C(O)—;

R$^1$ is selected from (C$_2$-C$_4$)alkyl, (C$_3$-C$_5$)cycloalkyl and methyl-substituted (C$_3$-C$_5$)cycloalkyl;

$R^2$ is selected from H, F, Cl, $OCH_3$ and CN;
$R^3$ is selected from H, F, $CHF_2$, $OCH_3$ and CN;
when X is —S(O)$_2$— then
  $R^4$ is selected from ($C_1$-$C_4$)alkyl, ($C_3$-$C_5$)cycloalkyl, $NH_2$ and NH($C_1$-$C_4$)alkyl, and $R_5$ is H; or
  $R^4$ and $R^5$ together are —$CH_2CH_2$— or —N($CH_3$)$CH_2$—; and
when X is —C(O)— then
  $R^4$ is selected from $NH_2$ and NH($C_1$-$C_4$)alkyl, and $R_5$ is H; or
  $R^4$ and $R^5$ together are —N($CH_3$)$CH_2$—.

2. The compound according to claim 1 of formula ($I^A$)

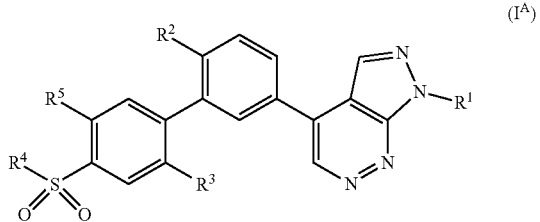

or a pharmaceutically acceptable salt thereof, wherein
$R^1$, $R^2$ and $R^3$ are as defined in claim 1 and
$R^4$ is selected from ($C_1$-$C_4$)alkyl, ($C_3$-$C_5$)cycloalkyl, $NH_2$ and NH($C_1$-$C_4$)alkyl, and $R_5$ is H; or
$R^4$ and $R^5$ together are —$CH_2CH_2$— or —N($CH_3$)$CH_2$—.

3. The compound according to claim 2, or a pharmaceutically acceptable salt thereof, wherein $R^4$ is ($C_1$-$C_4$)alkyl and $R_5$ is H.

4. The compound according to claim 3, or a pharmaceutically acceptable salt thereof, wherein $R^4$ is ethyl.

5. The compound according to claim 1 of formula ($I^B$)

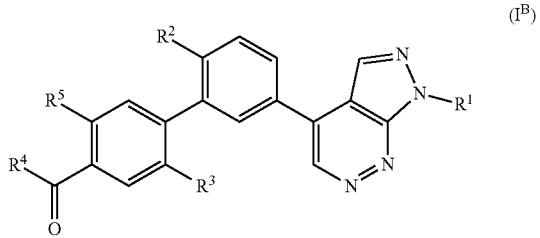

or a pharmaceutically acceptable salt thereof, wherein
$R^1$, $R^2$ and $R^3$ are as defined in claim 1 and
$R^4$ is selected from $NH_2$ and NH($C_1$-$C_4$)alkyl, and $R^5$ is H; or
$R^4$ and $R^5$ together are —N($CH_3$)$CH_2$—.

6. The compound according to claim 5, or a pharmaceutically acceptable salt thereof, wherein $R^4$ and $R^5$ together are —N($CH_3$)$CH_2$—.

7. The compound according to any one of claims 1 to 6, or a pharmaceutically acceptable salt thereof, wherein $R^1$ is ($C_2$-$C_4$)alkyl.

8. The compound according to claim 7, or a pharmaceutically acceptable salt thereof, wherein $R^1$ is ethyl.

9. The compound according to claim 8, or a pharmaceutically acceptable salt thereof, wherein $R^2$ is selected from H and F.

10. The compound according to claim 9, or a pharmaceutically acceptable salt thereof, wherein $R^2$ is F.

11. The compound according to claim 10, or a pharmaceutically acceptable salt thereof, wherein $R^3$ is selected from H and $OCH_3$.

12. The compound according to claim 11, or a pharmaceutically acceptable salt thereof, wherein $R^3$ is $OCH_3$.

13. The compound according to claim 1 selected from:
  4-(4'-ethanesulfonyl-6-fluoro-2'-methoxybiphenyl-3-yl)-1-ethyl-1H-pyrazolo[3,4-c]pyridazine,
  4-(4'-ethanesulfonyl-6-fluorobiphenyl-3-yl)-1-ethyl-1H-pyrazolo[3,4-c]pyridazine, and
  5-[5-(1-ethyl-1H-pyrazolo[3,4-c]pyridazin-4-yl)-2-fluorophenyl]-6-methoxy-2-methyl-2,3-dihydroisoindol-1-one,
  or a pharmaceutically acceptable salt thereof.

14. A pharmaceutical composition comprising a compound according to claim 13 and a pharmaceutically acceptable excipient.

15. A combination comprising a compound according claim 13 and a second pharmaceutically active agent.

16. The compound according to claim 13 for use in the treatment of pain.

17. The compound according to claim 13 for use in the treatment of epilepsy.

18. A method of treating pain comprising the administration to a subject in need of such treatment of an effective amount of a compound according to claim 13.

19. A method of treating epilepsy comprising the administration to a subject in need of such treatment of an effective amount of a compound according to claim 13.

* * * * *